US011209383B2

(12) United States Patent
Seker et al.

(10) Patent No.: US 11,209,383 B2
(45) Date of Patent: Dec. 28, 2021

(54) INTEGRATED ELECTROCHEMICAL DETECTION AND PURIFICATION OF NUCLEIC ACID BIOMARKERS

(71) Applicant: THE REGENTS OF THE UNIVERSITY OF CALIFORNIA, Oakland, CA (US)

(72) Inventors: Erkin Seker, Davis, CA (US); Joshua Hihath, Woodland, CA (US); Maria Marco, Davis, CA (US); Paul Feldstein, Sacramento, CA (US); Pallavi Daggumati, Emeryville, CA (US); Yuanhui Li, Davis, CA (US); Zimple Matharu, Davis, CA (US); Juan Artes Vivancos, Amstelveen (NL)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 404 days.

(21) Appl. No.: 16/176,877

(22) Filed: Oct. 31, 2018

(65) Prior Publication Data

US 2019/0137434 A1    May 9, 2019

Related U.S. Application Data

(63) Continuation of application No. PCT/US2017/030867, filed on May 3, 2017.
(Continued)

(51) Int. Cl.
*C12Q 1/6825* (2018.01)
*G01N 27/327* (2006.01)
(Continued)

(52) U.S. Cl.
CPC ....... *G01N 27/3276* (2013.01); *C12Q 1/6825* (2013.01); *C12Q 1/6834* (2013.01);
(Continued)

(58) Field of Classification Search
None
See application file for complete search history.

(56) References Cited

U.S. PATENT DOCUMENTS 5,759,773 A * 6/1998 Tyagi ............... C12Q 1/6813
435/6.12
2009/0050492 A1   2/2009 Alocilja
(Continued)

FOREIGN PATENT DOCUMENTS

WO    2012142003    10/2012

OTHER PUBLICATIONS

Ahangar et al., Biosensors and Bioelectronics, vol. 38, pp. 252-257, published online Jun. 7, 2012.*
(Continued)

*Primary Examiner* — Robert T. Crow
(74) *Attorney, Agent, or Firm* — O'Banion & Ritchey LLP; John P. O'Banion

(57) ABSTRACT

A biosensor platform apparatus and method are provided that can detect, purify and identify nucleic acid (DNA and RNA) biomarkers in complex biological fluids. The methods use a two-stage molecular based approach. The first stage screens for specific nucleic acid-based biomarkers in complex biological fluids by electrochemical detection of DNA:RNA hybridization and facilitates the removal of remaining complex media constituents. The first stage utilizes probes within a tunable nanoporous electrode. The second stage identifies the purified specific hybrids by single-molecule conductance measurements via break junction scanning. Identification can be assisted with a library of conductance
(Continued)

measurements. The methods can provide strain level information that can be used for identifying anti-microbial resistance in detected pathogens. Collection of RNA targets allows for biomarker detection and identification without the need for amplification and can provide information about the viability of the sample organism.

16 Claims, 7 Drawing Sheets

Related U.S. Application Data

(60) Provisional application No. 62/331,377, filed on May 3, 2016.

(51) Int. Cl.
*C12Q 1/6834* (2018.01)
*G01N 27/26* (2006.01)
*G01N 33/483* (2006.01)
*G01N 27/447* (2006.01)

(52) U.S. Cl.
CPC ......... *G01N 27/26* (2013.01); *G01N 27/3277* (2013.01); *G01N 27/44791* (2013.01); *G01N 33/483* (2013.01)

(56) References Cited

U.S. PATENT DOCUMENTS

| | | |
|---|---|---|
| 2010/0084276 A1 | 4/2010 | Stuart |
| 2013/0196323 A1 | 8/2013 | Hall |
| 2016/0054260 A1 | 2/2016 | Leburton |

OTHER PUBLICATIONS

ISA/US, United States Patent and Trademark Office (USPTO), International Search Report and Written Opinion dated Jul. 27, 2017, related PCT international application No. PCT/US2017/030867, pp. 1-13, claims searched, pp. 14-18.

Takmakov, Ivan et al., "Application of anodized aluminum in fluorescence detection of biological species", Anal Bioanal Chem (2006) 385: 954-958, vol. 385, No. 5, published online May 25, 2006.

Drossman, Howard et al., "High-Speed Separations of DNA Sequencing Reactions by Capillary Electrophoresis", Anal. Chem. 1990, 62, 900-903, vol. 62, No. 9, May 1, 1990.

Benck, Jesse D., "Substrate Selection for Fundamental Studies of Electrocatalysts and Photoelectrodes: Inert Potential Windows in Acidic, Neutral, and Basic Electrolyte", PLoS One, vol. 9, No. 10, e107942, pp. 1-13, Oct. 20, 2014.

Daggumati, Pallavi et al., "Sequence-Specific Electrical Purification of Nucleic Acids with Nanoporous Gold Electrodes", J. Am. Chem. Soc., vol. 138, No. 24, pp. 7711-7717, Jun. 22, 2016, published online May 31, 2016.

* cited by examiner

# INTEGRATED ELECTROCHEMICAL DETECTION AND PURIFICATION OF NUCLEIC ACID BIOMARKERS

CROSS-REFERENCE TO RELATED APPLICATIONS

This application claims priority to, and is a 35 U.S.C. § 111(a) continuation of, PCT international application number PCT/US2017/030867 filed on May 3, 2017, incorporated herein by reference in its entirety, which claims priority to, and the benefit of, U.S. provisional patent application Ser. No. 62/331,377 filed on May 3, 2016, incorporated herein by reference in its entirety. Priority is claimed to each of the foregoing applications.

The above-referenced PCT international application was published as PCT International Publication No. WO 2017/192737 on Nov. 9, 2017, which publication is incorporated herein by reference in its entirety.

STATEMENT REGARDING FEDERALLY SPONSORED RESEARCH OR DEVELOPMENT

This invention was made with Government support under 1231915, 1512745 and 1454426, awarded by the National Science Foundation. The Government has certain rights in the invention.

BACKGROUND

1. Technical Field

The technology of this disclosure pertains generally to pathogen screening methods and sensors, and more particularly to a sensitive sample-in-answer-out diagnostic platform and method for electrochemical detection and purification of target nucleic acids and rapid pathogen identification.

2. Background Discussion

Every year nearly a million Americans are diagnosed with sepsis. Sepsis is a severe systemic inflammatory response to an infection, which causes cellular and tissue damage leading to acute organ dysfunction. Sepsis-related mortalities range between 28% and 50%, due in part to the unexpected start and rapid progression of the condition. This high mortality rate clearly indicates that the ability to quickly and accurately detect the pathogens initiating the infection is still a major hurdle to effective medical intervention. In order to compensate for the delay in identifying these pathogens, patients are usually put on heavy doses of multi-drug treatments, which may further complicate the condition, lead to adverse effects on vital organs such as the liver, or interfere with other medical treatments that the patient is receiving.

The primary method for identifying the source of sepsis is based on microbial culture techniques (most commonly blood culture) followed by antimicrobial drug susceptibility testing. Detection of sepsis-inducing infections from blood cultures is usually performed with automated instruments that detect microbial growth by analyzing $CO_2$ release using fluorescent or colorimetric techniques. This technique has the benefit of measuring growth rather than providing an end-point microbial count, but it requires 20 mL to 40 mL of blood per venipuncture within a single blood culture order before initiating anti-infective therapy. Although blood cultures are the standard of care, the overall time to result is excessively long and keeps physicians from making rapid and appropriate treatment decisions. Therefore quick diagnostic assays obviating the need for sample purification and culture for pathogen enrichment steps are needed.

Newer approaches such as polymerase chain reaction (PCR) and matrix-assisted laser desorption ionization (MALDI)—time of flight (TOF) have been developed in an attempt to accelerate the turnaround time for microbial culture results. Unfortunately, despite the benefits associated with microbiological culture enhanced by molecular or mass spectrometry techniques, the turnaround times remains high and incompatible with early treatment algorithms and mass MALDI-TOF cannot distinguish between different pathogens in a positive blood culture. These delays are due to the time needed to grow pathogens in culture.

Nucleic acid-based biosensors have enabled sensitive detection of pathogenic targets in shorter time frames. One significant drawback to pathogen screening with a polymerase chain reaction procedure, for example, is that they are highly sensitive to PCR-inhibitors and other constituents of complex biological fluids that adversely affect sensor performance. Consequently, these devices typically require purified nucleic acids for amplification and analysis. This purification step is typically performed off of the device, thereby increasing sample-to-answer time as well as introducing contaminants.

Traditional benchtop (off-chip) processes for DNA extraction normally utilize phase separation, where proteins in the complex biological sample are denatured or aggregated, DNA is precipitated with alcohols or physio-adsorbed to a solid phase support, and DNA is finally recovered through centrifugation or elution.

However, detection in complex samples is still challenging due to the non-specific adsorption of proteins that may foul the sensor surface and lead to erroneous signals, hence nucleic acid purification from biological samples often remains as a crucial and laborious initial step.

Another major obstacle to realizing sample-in-answer-out platforms is the lack of seamless integration of sample preparation and analysis modalities. In order to achieve a complete sample-in-answer-out system, it is imperative to integrate sample preparation and detection modalities. While DNA capture via solid phase supports, such as ones created by packing microfluidic channels with silica beads or embedding the beads in sol-gel matrices, is more conducive to integration into miniaturized nucleic acid interrogation platforms, these devices still suffer from mechanical instability, including matrix shrinkage that compromises DNA extraction efficiency.

Accordingly, there is an urgent need for diagnostic assays that can shorten the lead time to a conclusive result that do not require cell culturing, sample purification, and nucleic acid amplification or purification. There is also a need for a rapid, miniaturized, diagnostic tool with the ability to detect directly from small volumes of a biological sample with high sensitivity and that is amenable to multiplexing and integration with electronics.

BRIEF SUMMARY

The diagnostic methods of the technology utilize nanoporous metal (np-Au) materials and single-molecule electrical conductance measurements, as part of a biosensor platform that can detect, purify and identify nucleic acids (DNA and RNA) in complex biological fluidics such as serum or digested cell lysate.

This is accomplished by utilizing a two-staged molecular-based approach where the first stage screens for specific pathogens at the genus/species level in complex biological fluids by electrochemical detection of DNA:RNA hybridization and allows for the removal of other complex media constituents.

This first stage simultaneously detects and purifies the oligomers of interest. The inherent nano-morphology of the nanoporous electrode allows for selective transport of nucleic acids into the pores of the sensing surface, while excluding other biomolecules, such as proteins and lysate debris, thereby eliminating the need for prior nucleic acid purification.

The second stage provides strain-level information by detecting the purified hybrid using single-molecule conductance measurements. This second stage employs moveable, nanostructured electrodes with sub-nanometer tips that can make contact to a single-molecule (DNA:RNA duplex), and measure its electrical conductance. The second stage preferably identifies the purified specific hybrid by single-molecule conductance measurement via break-junction based conductance measurements such as scanning tunneling microscopy (STM).

The electrochemical detection methods show sensitive detection for the target but are less sensitive for partially matched targets. The single molecule conductance measurements can distinguish even a single base mismatch and show sensitive detection in extremely low concentrations of hybrids. However, the first electrochemical step with np-Au surface helps to filter out the larger protein molecules present in the complex solution normally produce a large background signal in the break-junction measurements. The combination of the two techniques in the form of a 2-stage system enables the detection of target nucleic acids in complex biological samples and provides in situ validation to decrease false negatives and false positives.

The apparatus and methods can be illustrated in the context of sepsis pathogen identification. However, the apparatus and methods can be adapted to identify many different pathogens, as well as nucleic acid-based biomarkers (e.g., circulating nucleic acids for tumor identification and disease monitoring), in a variety of different biological samples (e.g., food, plant extracts, saliva, urine, lung lavage, etc.).

In the case of sepsis pathogen identification, infected blood samples are drawn from a patient and lysed and digested. The lysed and digested blood samples from sepsis patients are processed sequentially through the electrochemical-based and conductance-based platforms. The digest is then placed onto nanoporous metal foam electrodes that have been functionalized with single-stranded short DNA probe sequences which are complementary to a selected pathogen RNA sequences. Arrays of nanoporous conductive electrodes can be formed and each functionalized with a different probe sequence within a microfluidic system.

The nanoporous structure of the electrode surface allows the nucleic acid fragments from the digest to penetrate the pores of the electrode, while non-complementary nucleic acids flow through and adsorbed proteins and other biomolecules and lysate debris are excluded. Hybridization events between the probe and target molecules will invoke an electrochemical signal indicative of the presence of a pathogen.

Following a washing step to remove the excluded biofouling molecules, the hybridized molecules will be electrokinetically eluted from the porous network via microfluidics. This first stage will detect pathogens without prior nucleic acid extraction and yield purified nucleic acids for further processing.

The nanoporous conductive thin film electrodes are amenable to seamless integration with microfluidics and other microchip components to build complete sample-in-answer-out platforms. Leveraging these features, the two-part purification approach enables both the electrochemical detection of DNA targets of interest in the presence of complex media as well as subsequent electro-kinetic release of the DNA-DNA hybrids free of contaminants (e.g., serum macromolecules and mismatched DNA fragments) for additional downstream analysis in the second stage.

The purified DNA:RNA hybrids are capable of identifying specific pathogens and serotypes (e.g. anti-microbial resistant strains). The hybrids released from the electrode are then interrogated by capturing them between two atomically-sharp electrodes for conductance measurements. Since each sequence has a unique electrical conductance value, this second stage provides the ability to detect mismatched hybrids.

Contrary to the traditional conductance-based electrochemical biosensors where scattering and changes in carrier concentration dominate the signal, in the case of single-molecule conductance measurements, the charge is transported through the target molecule. Because of this binary process (molecular junction vs. tunneling gap) the conductance will change by many orders of magnitude when a molecule is present. Furthermore, charge transport through short (~5 nm) duplexes is dominated by quantum mechanical processes, and as such the order of the bases is important (i.e. two different sequences with the same G:C content should have different conductance values).

The resulting conductance signatures for specific strains and serotypes can optionally be accumulated into to a reviewable library. This information can be used in the future to identify the presence of specific RNA sequences in subsequent purified samples to improve the ultimate sensitivity and specificity of the assay. This also allows minute sequence nuances to be revealed, and thereby provide strain-specific pathogen information and limit false-positive detections.

The combination of the features of both stages yields a system that offers (i) excellent signal-to-noise performance because there is a large difference in electrical current between a molecule binding event and absence of a molecule; (ii) low limits of detection because of the single-molecule level sensitivity of the technique; (iii) unprecedented selectivity allowing small sequence differences to be detected to identify pathogens that are not susceptible to standard anti-microbial treatments; and (iv) the ability to identify multiple targets simultaneously.

The technology provides a versatile and scalable assay for rapid identification of pathogens in minimally-processed biological fluids, thereby significantly shortening the time to a conclusive diagnosis for sepsis etc. This in turn will prevent non-specific pharmaceutical loading of sepsis patients and allow for the identification of a variety of pathogen-specific treatment regimens.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only.

DETAILED DESCRIPTION

Referring more specifically to the drawings, for illustrative purposes, embodiments of methods for pathogen nucleic acid purification and identification are generally shown. Referring more specifically to the drawings, for illustrative purposes, embodiments of methods for pathogen nucleic acid purification and identification are generally shown. Several embodiments of the technology are described generally in FIG. 1 through FIG. 3 to illustrate the apparatus and system characteristics and functionality. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

Generally, a two stage microfluidic apparatus is used to illustrate the technology that has a nanoporous conductive first stage electrode and a second stage break-junction with moveable, nanostructured electrodes with sub-nanometer mechanical resolution that can make contact with a single-molecule (DNA:RNA duplex) and measure the conductance.

Although the methods are demonstrated in the context of sepsis pathogen purification and identification, the apparatus and methods can be adapted and applied to many other pathogens and nucleic acid-based biomarkers in a variety of different biological samples.

Figure 1:
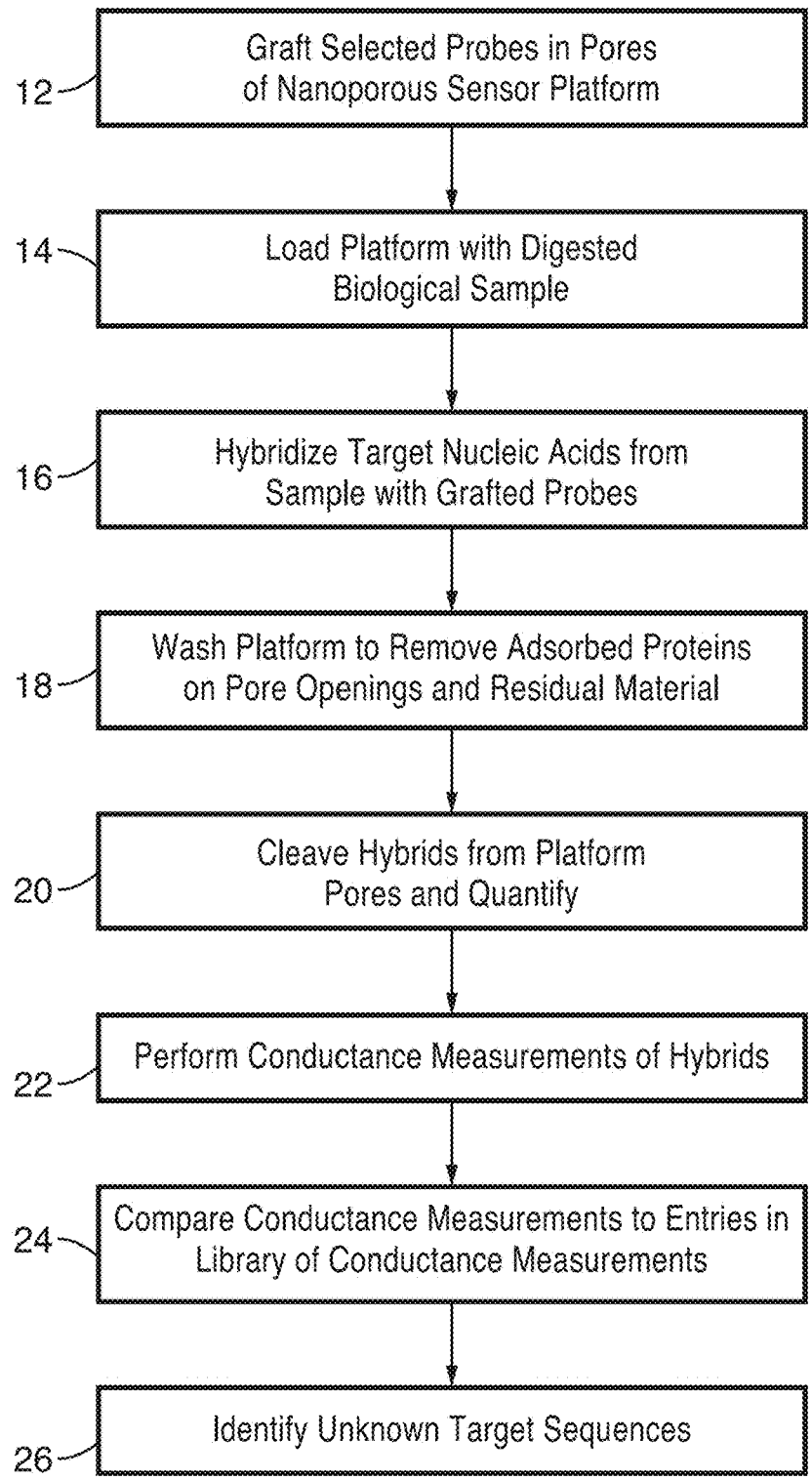
FIG. 1 is a functional block diagram of a method for target nucleic acid capture, purification and identification using a two stage framework according to one embodiment of the technology.

Turning now to FIG. 1, a flow diagram of one embodiment of a method 10 for pathogen nucleic acid identification is shown schematically. Initially, an apparatus is provided with a first stage electrode with tunable nanoscale morphology. The first stage electrodes are preferably made from a nanoporous metal such as nanoporous gold (np-Au). Nanoporous gold can be integrated into multiple electrode arrays via conventional micro-fabrication techniques. The morphology of each electrode can be tuned by electrochemical coarsening, electro-annealing or laser treatment (i.e. with in situ laser annealing).

For example, multiple np-Au electrode arrays (MEAs) can be fabricated on glass slides using conventional microfabrication techniques. In one technique, patterns of gold-silver alloy (precursor to np-Au) can be sputter-deposited to form a layer and then treated with a photolithographic lift-off process.

Np—Au electrode layers are then produced by simply immersing the structures in nitric acid, where the porous morphology can be readily tuned by thermal treatment in an oven or by in situ laser annealing to produce different morphologies on a single chip. These capabilities allow for the scalability of the electrodes to larger arrays and the ability to tune-in specific pore morphologies to optimize electrode nanostructure on sensor performance. The tuning of the Np—Au electrode morphology allows for biofouling-resilient sensor performance, enhanced limit of detection, and tunable dynamic range.

Figure 2A:
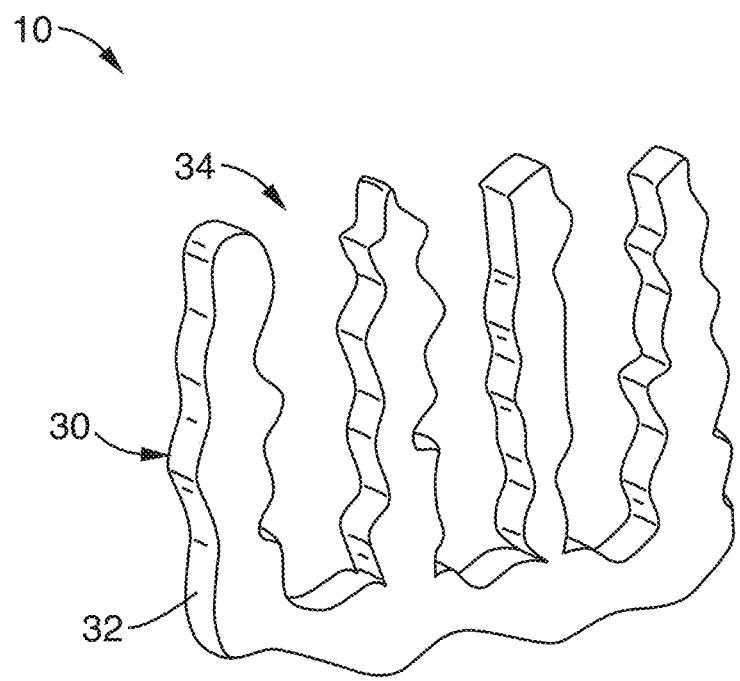
FIG. 2A is a schematic side perspective sectional view of open pores of a nanoporous electrode of stage 1 according to the technology.

The nanoporous sensor platform functionalization is also shown schematically in FIG. 2A through FIG. 2D. The sensor electrode platform generally has conductive walls 30 with surfaces 32 and open pores 34 as shown in FIG. 2A.

Figure 2B:
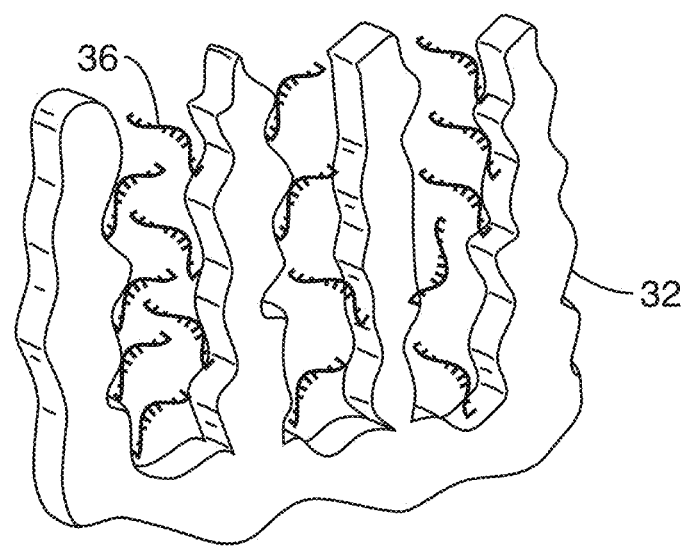
FIG. 2B is a schematic side perspective sectional view of pores of a nanoporous electrode with nucleic acid probes grafted to the inside of the pores of FIG. 2A.

Selected nucleic acid probes 36 are then grafted to the wall surfaces 32 of the pores 34 of the first stage nanoporous metal electrode at block 12 of FIG. 1 and illustrated at FIG. 2B. The electrodes are preferably individually addressable for simultaneous electrochemical interrogation. The probes 36 are preferably grafted to the surface 32 of the pores by a thiol bond. For example, the probes can be thiolated DNA that is complementary to a selected target RNA. However, other types of probe linkers such as selenol groups or amines could be used in the alternative.

The grafted probes can also be PNA (peptide nucleic acid) or LNA (locked nucleic acid) structures that are bound to a nanostructured electrode surface. The probes 36 are selected based on the particular target nucleic acid 40 of interest. Target nucleic acid molecules 40 are preferably about 10 nM to 200 nM in length. The target molecules 40 are typically markers that are unique to a nucleic acid-based biomarker presence in a sample.

Although a single nanoporous platform with a single nucleic acid probe is used to illustrate the system, it will be understood that many different nanosensor platforms with many different or redundant nucleic acid probes can be formed in an array.

The nanoporous sensor platforms that are functionalized at block 12 are then loaded with a digested biological sample containing target molecules 40 at block 14.

Figure 2C:
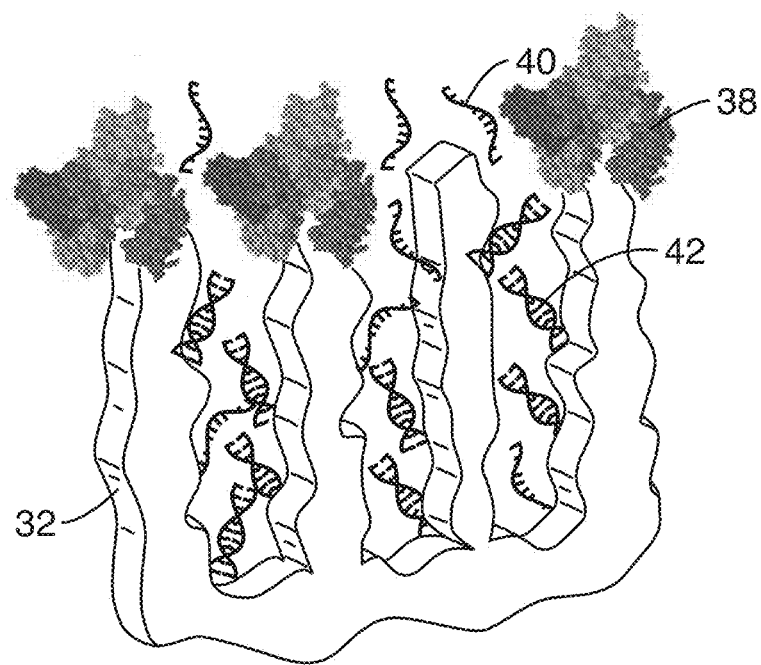
FIG. 2C is a schematic side perspective sectional view of pores of a nanoporous electrode with grafted nucleic acid probes hybridized with target molecules and adsorbed proteins excluded from the pores as well as unbound nucleic acids flowing through the pores.

At block 16 of FIG. 1, the target molecules 40 that are present in the digested sample cells can percolated through the pores 34 of the sensor electrode platform and hybridize with the grafted probes 36 to form a hybrid 42 as shown in FIG. 2C. A decrease in the peak of the electrochemical current in the presence of target molecules 40 signifies successful probe-target hybridization 42. For very low pathogen counts (e.g., <10 CFU/mL), the sensor performance can be greatly influenced by the time it takes for a pathogen nucleic acid target to come in contact with the probes of the sensing electrode. Therefore, microfluidics and micro-features on the substrate may be employed to increase the probability of electrode-target interactions.

Larger molecules such as proteins 38 may adsorb to the upper surface of the electrode and pore openings and other residual digested material may be present on the surface. The sensor electrode platform is then washed at block 18 to remove the adsorbed proteins and residual materials. This washing preferably leaves only the hybrids 42 bound to the surfaces 32 of walls 30 of the electrode platform.

Figure 2D:
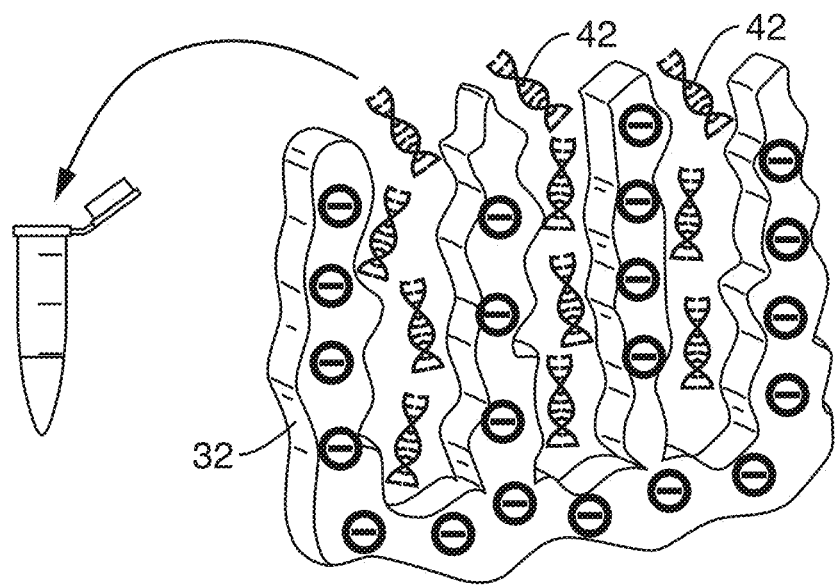
FIG. 2D is a schematic side perspective sectional view of pores of a nanoporous electrode after the removal of adsorbed proteins and electro-cleaving to release the hybrids for subsequent analysis.

The hybrids 42 are cleaved from the pores of the electrode platform and collected and optionally quantified at block 20 of FIG. 1. Subsequent electrochemical cycling at negative potentials detaches the immobilized hybrid from the electrode surface as shown in FIG. 2D. No peak in electrochemical current will be observed following the desorption of the hybrids 42. The electrochemical desorption of probe-target hybrid duplexes should allow for selective elution of different probe-target pairs by modifying the linker chemistry (e.g., using selenol groups instead of thiol groups for certain molecules on the surface). Molecules with selenol groups can be cleaved in a different potential window thus enabling selective cleaving.

Accordingly, the nanoporous electrodes can be used for the capture and electro-kinetically release the hybridized nucleic acid targets. The mechanism of biofouling-resilience is that the debris in biological samples, such as proteins, is too large to go through the platform pores while the short, fiber-like, digested nucleic acids can penetrate the porous network. In this scenario, upon capture of the target molecules, the top surface of the electrode may be covered with biomolecules. Due to the optimal pore size and biofouling-resilient nature of the selected nanoporous metal platform morphology, only specific target nucleotides will be able to go into the pore and bind with the sensing probe DNA. The bigger protein molecules blocked by the surface will be collected. However, there might be a chance that some of the smaller non-specific biospecies make their way inside the porous structure. In order to wash them out, bio-surfactants such as sodium dodecyl sulfate, Triton-X, or Tween-20 may be employed. Thus the large biomolecules can be washed away and the captured nucleic acids can be selectively released by electrochemically-cleaving the thiol-gold bond.

Figure 3:
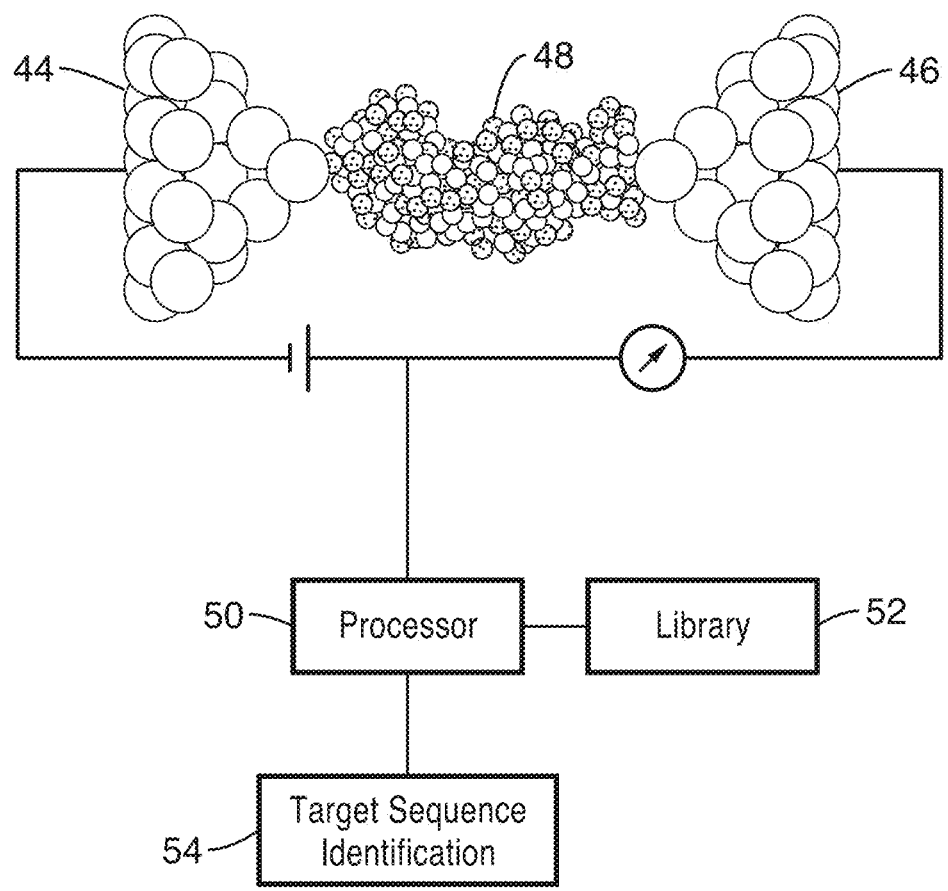
FIG. 3 is a schematic functional view of the second stage single-molecule conductance measurements, library and identification according to one embodiment of the technology.

At stage two of the process, conductance measurements of the collected hybrids are made at block 22 of FIG. 1. Single-molecule conductance measurements of the hybrids are conducted for species and strain-level identification. Referring also to FIG. 3, conductance measurements oligonucleotide duplex hybrids are preferably performed with a break junction technique. Break junction techniques are ideally suited to the task of identifying when only a single-molecule is bound between two electrodes. The measurements proceed by bringing one atomically sharp electrode 44 into contact with a second electrode 46 in the presence of the molecules 48 of interest. In one embodiment, the probe can have a linker (e.g. amines, selenols or thiols) on each terminus to provide for the binding to the electrodes. Once contact is made between the two electrodes, the tip is withdrawn until the current reaches the resolution of the current amplifier (~pA). If molecules bind between the two electrodes during the separation process, then steps occur in the current vs. distance trace. By repeating this process hundreds or thousands of times, it is possible to perform a statistical analysis of the results to determine the most probable conductance of a single molecule junction. Although the system is capable of single-molecule detection, the formation of a single junction will not be relied on to identify the presence of the target species. Instead, a statistical approach will preferably be used to verify the presence of the RNA target in solution, and to limit the number of false negatives and positives.

In contrast to traditional conductance-based biosensors where scattering and changes in carrier concentration dominate the signal, the charge is transported through the target molecule in the case of single-molecule conductance measurements. Because of this binary process (molecular junction vs. tunneling gap) the conductance will change by many orders of magnitude when a molecule is present. Furthermore, charge transport through short (~5 nm) duplexes is dominated by quantum mechanical processes, and consequently the order of the bases is important (i.e. two different sequences with the same G:C content should have different conductance values, for example).

Therefore, the system can detect small differences in sequence and can identify multiple targets simultaneously. The conductance of oligonucleotides has been demonstrated to be extremely sensitive to the length, sequence, and single base mismatches. For example, when the alternative target is hybridized to the DNA probe, the mismatch can change the conductance by approximately 25%. Thus, the technique is capable of providing serotype level information about the target and therefore is capable of identifying anti-microbial resistant strains, for example.

In the embodiment of FIG. 3, the apparatus and conductance measurements are controlled by a processor 50 with programming instructions. The processor 50 can also process signals and display and store sensor results. The conductance of hybrids from a sample can be compared with conductance features of a perfectly matched DNA:RNA hybrid as well as conductance values of known hybrid mismatches from a library 52 of conductance values at block 24 of FIG. 1. The entries of the optional library of conductance values 52 for specific pathogens can be compared to determine the presence of any hybrid mismatches from the sample. For example, the sensor in this embodiment may be capable of identifying a large database of sepsis-related pathogens, to be used after electro-kinetic or other purification protocols have been applied to increase the absolute level of detection and to allow sub-species level identification 54 to inform treatment protocols.

In one embodiment, different libraries can be developed directed to one or a group of pathogens. For example, a library of conductance values for sequences capable of identifying sepsis-related microbes can be developed based on identified highly expressed sequences (e.g. ribosomal RNA) that are specific to the each of the pathogens of interest, as well as sequences that indicate viability.

A library of conductance values 52 of these sequences and their closely related sequences (mismatches) using synthetic oligonucleotides can be created. Once the target sequences have been identified the next step may be the development of synthetic RNA target and DNA probe sequences, to rapidly determine the conductance values of specific sequences that are capable of directly identifying the targets of interest. In addition to identifying appropriate species for detection, it may also be important to select appropriate gene transcripts for identification.

Finally, the target sequence is identified 54 by the processor 50 and displayed and at block 26 of FIG. 1. If the conductance measurements of the target sequence are not in the library, then the measurements for that sequence can be entered for future use.

In an alternative embodiment, the targets from the sample digests are hybridized with the target probes in solution. The probe preferably has a thiol bond on each terminus to permit binding to the surfaces of pore walls of the nanoporous electrode. The hybrids that were formed in solution are then applied to the nanoporous electrode platform and the hybrids bind to the surface. The electrode is then washed to remove any material that is not bound to the walls. The presence of hybrids on the nanoporous electrodes can be detected with electrochemistry prior to release. The collected target-probe hybrids can also be analyzed with fluorescence to determine hybrid concentration, absorbance to determine a DNA-to-protein concentration ratio, and capillary electrophoresis to determined hybrid size and purity.

In another alternative embodiment, a variety of different types of probe molecules can be provided with each probe type coupled to a chemical linker that has a different affinity to the electrode. The different probe hybrids can then be selectively eluted by applying different electrochemical potentials over time. For example, a first set of target probes are anchored to the nanoporous electrode with a thiol group linker and a second set of a different target probe are anchored to the nanoporous electrode with a selenol group linker. After exposure to the sample and target-probe hybridization, the first target-probe hybrids are released from the nanoporous electrodes by electrochemically cleaving the thiol linker of the first target probes and the hybrids are collected. The second target-probe hybrids are then released from the nanoporous electrodes by electrochemically cleaving the selenol linker of the second target probes and then collected. Suitable chemical linkers will reversibly bind to the electrode and include a selenol group linker, an amine group linker and a thiol group linker etc.

The technology described herein may be better understood with reference to the accompanying examples, which are intended for purposes of illustration only and should not be construed as in any sense limiting the scope of the technology described herein as defined in the claims appended hereto.

Example 1

In order to demonstrate the operational principles of the apparatus and the capture and identification methods, a testing apparatus was fabricated with a structure and two-stage processing steps shown generally in FIG. 1 through FIG. 3.

For the first stage, electrodes of nanoporous gold (np-Au) were produced to enable both detection of specific target sequences in a complex biological sample and their subsequent purification. In this demonstration, the np-Au electrodes were modified with 26 mer DNA probes (via thiol-gold chemistry) that enabled sensitive detection and capture of complementary DNA targets in the presence of complex biological media (fetal bovine serum) and other interfering DNA fragments in the range 50 to 1500 base pairs. Upon target capture, the non-complementary DNA fragments and serum constituents of varying sizes were washed away with buffer. Finally, the surface-bound DNA-DNA hybrids were released by electrochemically cleaving the thiol-gold linkage and the hybrids were iontophoretically eluted from the nanoporous matrix. Then optical and electrophoretic characterization of the analytes before and after the detection-purification process revealed that low target DNA concentrations (80 pg/µl) can be successfully detected in complex biological fluids and subsequently released to yield pure hybrids free of polydisperse digested DNA fragments and serum biomolecules.

It was demonstrated that this multifunctional platform performed as a seamless integration of detection and purification of DNA biomarkers of pathogens and diseases in a miniaturized diagnostic device. In this demonstration, a homemade Teflon cell was utilized to carry out electrochemical measurements with a Gamry Reference 600 potentiostat. Np—Au and planar Au electrodes with foot print of 0.15 $cm^2$ were employed as working electrodes while platinum wire and Ag/AgCl electrodes were used as counter and reference electrodes respectively.

Np—Au gold films were prepared by sputter deposition and subsequent dealloying. Briefly, glass cover slips were cleaned in piranha solution, composed of 1:4 volumetric ratio of hydrogen peroxide (30%) to sulfuric acid (96%), rinsed in deionized (DI) water, and dried under nitrogen flow prior to metal deposition. Metal deposition was carried out using a magneto-sputtering system. First, a 160 nm-thick chrome layer was sputtered at 300 W to promote adhesion between glass and the subsequent metallic layers. Next, 80 nm-thick seed layer of gold was sputtered at 400 W and finally silver and gold were co-sputtered at 100 W and 200 W respectively to obtain a 600 nm-thick alloy layer. All depositions were performed successively under argon ambient at 10 mTorr. The composition of the alloy was 64% Ag and 36% Au (at. %) as determined by X-ray energy dispersive spectroscopy (EDS), (Oxford Instruments). The samples were then dealloyed in 70% nitric acid at 55° C. for 15 minutes to produce the np-Au films and then rinsed with DI water. The residual silver in np-Au samples after dealloying was estimated to be ~8% (atomic %) via EDS. Planar gold (pl-Au) electrodes were also fabricated by sputter-depositing a 50 nm-thick chrome adhesion layer followed by 250 nm-thick gold film onto piranha-cleaned glass cover slips. Top and cross-sectional images of np-Au electrode were captured via scanning electron microscope (FEI Nova NanoSEM430) at 100 kX magnification.

The np-Au and Au electrodes were cleaned in dilute (1:4) piranha solution for 20s prior to functionalization. The electrodes were then incubated in 25 mM phosphate buffer (PB), containing 2 µM thiolated probe DNA and 50 mM $MgCl_2$ for 15 hours at room temperature. 1 mM mercaptohexanol (MCH) prepared in PB was used as back-fill agent to passivate the surface that is not covered by probe DNA. The electrodes were thoroughly rinsed with PB to remove non-specifically bound DNA. DNA functionalized electrodes were incubated in 150 µl of 20 µM methylene blue (MB) prepared in 1× phosphate buffered saline (PBS) for control measurements and in 1×PBS containing or 10% fetal bovine serum (FBS) for complex media experiments for 10 minutes. 1×PBS was obtained from Corning and has a composition of 137 mM NaCl, 2.7 mM KCl, 10 mM $Na_2HPO_4$, and 1.8 $KH_2PO_4$ with a pH of 7.4. FBS (heat inactivated) was obtained from Life technologies. Unbound MB molecules were removed by washing with PB. Following which the electrode was placed inside a custom-built Teflon electrochemical cell and 1×PBS or 1×PBS containing 10% FBS was used for as the electrolyte for measurements. Probe-modified electrode was interrogated with different concentrations of target DNA. The electrode was incubated with desired target DNA prepared in PB containing 50 mM $MgCl_2$ or with the addition 10% FBS (complex media experiments) for 35 minutes at 37° C. Non-specifically bound target molecules were removed by PB rinse.

In order to characterize the platform, a unique 26 mer housekeeping region of the DNA sequence of tobacco mosaic virus (TMV) was used as a target sequence. The np-Au electrodes were functionalized with thiolated ssDNA (26 mer) specific to the target of interest (i.e., TMV). The 26 bp DNA sequences were purchased from Integrated DNA Technologies, USA. The 5'end of ssDNA probe was modified with a C6 linker and thiol group.

The total number of grafted probes was estimated to be $4.3 \times 10^{12}$ molecules, which translates into a grafting density that is 10 times that of its planar gold counterpart.

The sensor was then challenged with target DNA spiked in FBS solution to simulate a complex environment. The electrode was challenged with a complex mixture (FBS solution (10%) spiked with specific 26 mer target DNA and/or DNA digests containing several DNA fragments with strand length of 50 bp to 1500 bp) with a loading concentration of 300 nM (2.4 ng/μl).

Probe grafting and target hybridization were electrochemically quantified using the MB-DNA reduction peak obtained via square wave voltammetry (SWV). All SWV measurements were performed in 1×PBS containing 10% FBS over the potential range 0 to ~0.5 V with an amplitude of 40 mV, step size of 4 mV and frequency, 18 Hz for np-Au and 60 Hz for planar Au. Electrochemical cleaving was done using cyclic voltammetry (CV) with 25 mM phosphate buffer as the electrolyte.

Methylene blue (MB) redox marker was used for quantifying the extent of target hybridization. Methylene blue was used as a redox marker for electrochemical DNA detection and quantification due to its reaction-limited nature, its ability to permeate the porous structure before being fully depleted at the top surface and its ability to discriminate dsDNA from ssDNA.

This was followed by washing the FBS constituents followed by electrochemical cleaving to release the thiol-bound hybrids via cyclic voltammetry (CV). The onset of the thiol bond reduction typically occurs around −0.65 V, but it has been shown that desorption of surface-bound thiolated molecules happens with much higher efficiency at −1.3 V. In order to ensure complete removal of the surface-bound hybrids and to minimize their re-adsorption, a CV was used in the range of 0 to −1.5 V at scan rates of between 10 mV/s to 50 mV/s. Even though the release of the hybrids from a planar gold surface is almost instantaneous, transport of the desorbed hybrids through the porous np-Au structure was hindered due to surface-molecule interactions and tortuosity of the np-Au electrode. Desorption and elution of hybrids was further confirmed by adding PicoGreen (Thermo Fisher Scientific), a dsDNA quantitation fluorescent dye, to the eluted hybrids. The concentration of the eluted hybrids was then determined using a fluorescent plate reader (Nanodrop 3300).

The second stage electrical conductance measurements were performed by moveable, nanostructured electrodes with sub-nanometer tips that can make contact to a single-molecule (DNA:RNA duplex). A STM-break junction technique was used to measure the conductance of the DNA:RNA hybrids. A layer of 130 nm of gold was coated on mica using the electro-beam evaporation method and utilized as the STM substrate. The substrate was flame annealed prior to use. The STM tip was prepared by cutting a 0.25 mm gold wire, which was then coated with Apiezon wax afterwards to reduce leakage current below 10 pA. For the measurement, the DNA:RNA hybrid elution obtained from the electrochemical cleaving was directly added onto the gold substrate. During the experiment, the tip was first brought toward the substrate and once the current saturated, it was retracted until the current reached the minimum. This break junction process ensured probability of forming the junction with the hybrid linked in between the tip and substrate. During the retraction process, thousands of the current data were recorded. 10% of the recorded data showed a step in the trace which represented the conductance of the hybrid.

Accordingly, the sensor platform leverages the unique features of np-Au electrodes (i.e., biofouling resilience, lower limit of detection) to achieve integrated detection and purification of target DNA for further downstream bioanalytical analyses. The operations were performed in various environments, such as phosphate buffer, fetal bovine serum, and digested RNA fragments from E. coli cells. For all of these environments, it was possible to detect a signal on both stages, indicating this two-tiered, molecule-based approach is capable of providing effective nucleic-acid sensors.

Example 2

To further demonstrate the effectiveness of the apparatus and system in simple and complex environments, two-stage devices were prepared and evaluated under different conditions. For the electrochemical signal evaluations, prepared DNA functionalized nanoporous electrodes were incubated in 20 μM methylene blue (MB), a DNA hybridization indicator, prepared in 1× phosphate buffered saline (PBS) and placed inside a custom-built Teflon electrochemical cell. Square wave voltammetry (SWV) was used to investigate the reduction of MB which was the indicator of DNA immobilization.

For detection in complex environment evaluations, the target RNA was spiked in 10% fetal bovine serum (FBS) or digested RNA from E. Coli in one setting. The RNA sample was digested with RNase T1 enzyme after extracting it from the sliced E. Coli cell. The sample contained different lengths of RNA fragments along with the target RNA and other proteins. The probe modified np-Au was incubated with target solution for 35 minutes at 37° C. for target hybridization. The hybridized DNA:RNA molecules were cleaved from the np-Au surface by the application of a negative potential via cyclic voltammetry.

Figure 4A:
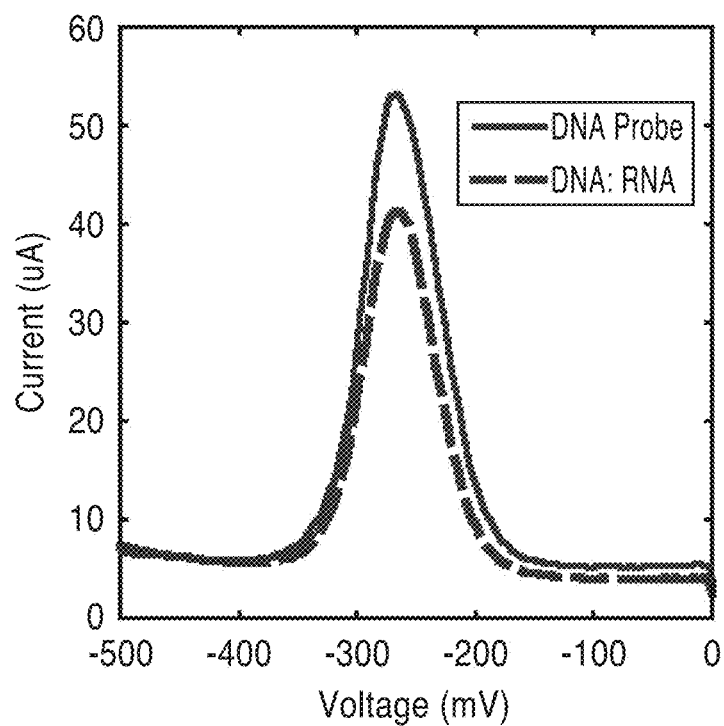
FIG. 4A is a graph of SWV signals of probe DNA and in-situ DNA:RNA hybridization in a simple media.
Figure 4B:
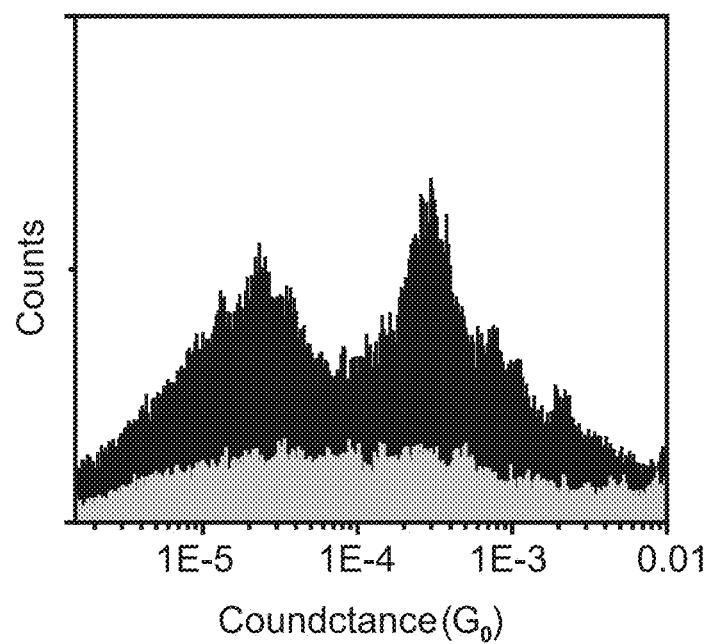
FIG. 4B is a graph of single-molecule conductance measurements of the released DNA:RNA hybrids.

To investigate the conductance of DNA:RNA hybrids, preliminary STM experiments were performed in phosphate buffer solution with perfect match and single mismatch hybrids. FIG. 4A is a graph of in-situ hybridization at the np-Au surface detected by SWV in a plain phosphate buffer solution. FIG. 4A shows signals obtained for the probe DNA and target hybridization signals. After this measurement, the samples were washed and then released for single-molecule conductance characterization. Conductance measurements of the DNA:RNA hybrids obtained after the first electrochemical stage are shown in FIG. 4B.

The conductance measurement for the DNA:RNA (perfect match) duplex revealed a conductance peak at $3 \times 10^{-4}$ $G_0$ ($G_0$ is the quantum conductance, 77.5 μS), which confirms the presents of duplex in the solution However, presence of a single base mismatch in the duplex shifts the peak towards $6 \times 10^{-5} G_0$ from $3 \times 10^{-4} G_0$ due to change in the conductance of the duplex. The occurrence of a peak at $3 \times 10^{-4}$ $G_0$ is consistent with the peak obtained in buffer and confirms the presence of the hybrid. Thus, the 2-pass process not only purifies the target RNA in a complex environment but also self-confirms the detection results with two different detection methods.

Typical complex environments have several proteins that may contribute to a high background signal in the break-junction measurements. Consequently, the first stage of the 2-stage process filters out the unwanted proteins and longer RNA fragments at the np-Au electrode surface via electrochemistry.

Figure 5A:
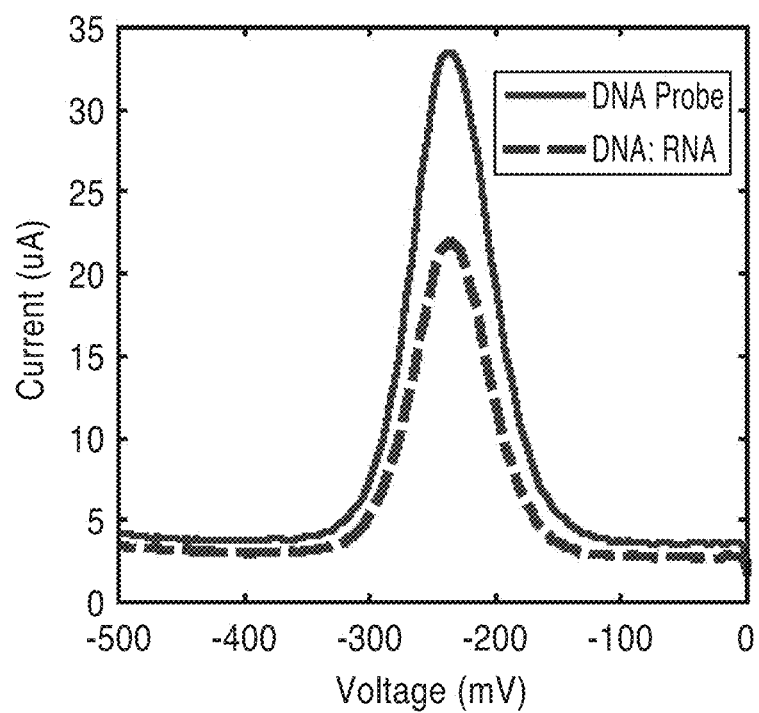
FIG. 5A is a graph of SWV signals of probe DNA and in-situ DNA:RNA hybridization in fetal bovine serum (FBS) media.
Figure 5B:
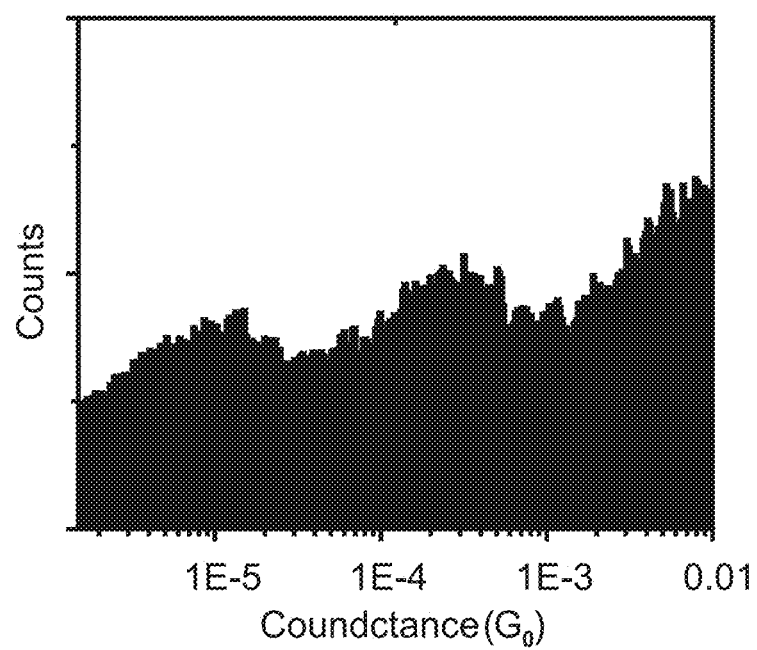
FIG. 5B is a graph of single-molecule conductance measurements of the released DNA:RNA hybrids

In-situ hybridization of single stranded *E. Coli.* DNA probes at the np-Au surface was detected by SWV in fetal bovine serum (FBS) is shown in FIG. 5A. FIG. 5A shows the SWV signals obtained for both probe DNA and target hybridization. In this case, a known a concentration of target RNA (300 nM) was prepared in 10% FBS solution. Hybridization of probe DNA and target RNA resulted in a decrease SWV signal by 35%. This step insures sieving of bigger protein molecules, present in FBS (e.g. BSA), via the nanopores of np-Au, while, the short specific target RNA molecules penetrates through the porous network and hybridize with the immobilized probe DNA. The large biomolecules in serum and un-hybridized DNA fragments were then washed away using PB several times.

The captured DNA:RNA hybrids were then released by electrochemical cleaving of the thiol-gold bond via application of negative potential. For this the DNA:RNA np-Au electrodes were cycled in PB in the potential range of 0 to −1.5V. This step ensures cleaving of hybrids off the Au surface and their diffusion out of the porous network. The DNA-RNA hybrids were eluted in PB and further used for the break-junction measurements.

To further prove the advantage of the 2-stage process, experiments excluding the first electrochemical purification stage. Hybridization of digested RNA fragments, which includes the target sequence, was conducted with the DNA probe in the buffer solution. Because of the high background signal (possibly due to RNase, RNase inhibitor and other proteins), it is difficult to distinguish the hybrid conductance peak at $3 \times 10^{-4} G_0$.

A further demonstration of the detection in a real complex environment was made with the use of digested RNA samples obtained from *E. Coli* cells. The final sample contained several lengths of the RNA, RNase and RNase inhibitor. The 2-stage system separated the targets from the non-specific fragments and the other proteins selectively obtained the perfect match which was further confirmed by the conductance measurements via STM.

SWV signals for probe DNA modified np-Au electrode and signal from real *E. Coli.* Sample that was spiked with 300 nM of target RNA were obtained. Hybridization of target RNA present in the complex sample with the probe DNA on the np-Au surface resulted in a decrease of SWV signal by 56%. After the target hybridization, the sensor surface was washed several times with PBS and the captured hybrid was cleaved via electrochemistry as explained above. The single molecule conductance measurement performed with eluted hybrid gives conductance peak at $3 \times 10^{-4} G_0$, confirming the presence of the hybrid in the electrochemically purified solution.

Titration experiments also demonstrated the sensitivity of single molecule conductance platform. Even with only a small number of molecules present in the solution (on the order of 100), a reliable conductance signal can still be obtained.

Figure 6A:
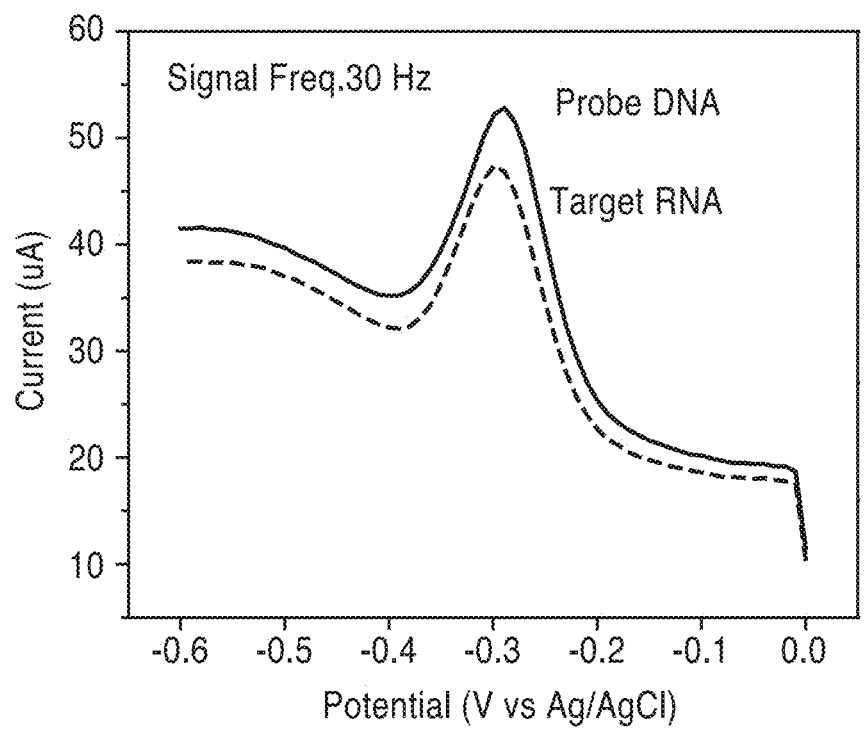
FIG. 6A is a graph of SWV signals of probe DNA and in-situ DNA:RNA hybridization in a whole blood media.
Figure 6B:
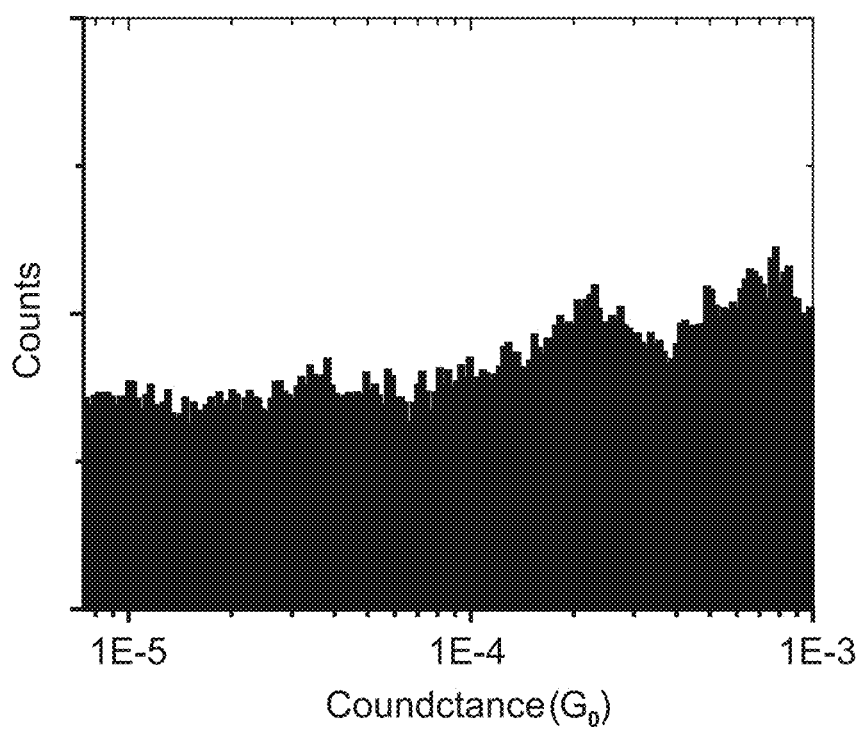
FIG. 6B is a graph of single-molecule conductance measurements of the released DNA:RNA hybrids.

The graph of FIG. 6A shows the in-situ hybridization of probe and target nucleic acids at np-Au surfaces detected by SWV in a Suinae whole-blood solution. The samples are washed and then the hybrids are released after the measurements shown in FIG. 6A. Single molecule conductance measurements of the DNA:RNA hybrids obtained after the first stage are depicted in the graph of FIG. 6B. The occurrence of peak at $3 \times 10^{-4} G_0$ demonstrates that the DNA:RNA hybrids can still be identified starting from a complex sample and environment using the system.

In summary, the two-stage detection platform will (i) directly detect pathogen nucleic acids from whole samples; (ii) purify nucleic acids of the detected pathogens; and (iii) provide sequence-dependent conductance values for different biomarker DNA:RNA duplexes. The sensor apparatus can be adapted to identifications in many different settings through the selection and synthesis of capture probe sequences such as the detection of nucleic acid markers of pathogens in digested blood lysates. In addition, the porous sensor platform morphology can be exploited to release the captured target nucleic acids after a protein wash. Nucleic acid purification via electrochemical intervention will normally produce hybrids with high enough purity for subsequent analysis via conductance or, if necessary, PCR or sequencing. The focus on RNA will not only allow biomarker detection, but will also give information about the state (e.g., viability) of the source organism. RNA will also circumvent the need for amplification. The molecular conductance approach can provide strain-level information that can be used for identifying any anti-microbial resistance in the detected pathogens and maximize the detection sensitivity.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used synonymously to denote a device capable of executing the instructions and communicating with input/output interfaces and/or peripheral devices, and that the terms processor, hardware processor, computer processor, CPU, and computer are intended to encompass single or multiple devices, single core and multicore devices, and variations thereof.

From the description herein, it will be appreciated that that the present disclosure encompasses multiple embodiments which include, but are not limited to, the following:

1. A method for detection and purification of nucleic acids from complex biological samples, the method comprising: (a) selecting at least one target and corresponding probe; (b) forming target-probe hybrid duplexes from targets from a sample; (c) capturing hybrid probe duplexes on nanoporous metal electrodes; (d) washing the nanoporous electrodes and captured target-probe hybrids to remove any sample parts that are not bound to the target probes; (e) releasing and eluting washed target-probe hybrids from the nanoporous electrodes; and (f) performing conductance measurements of the target-probe hybrids.

2. The method of any preceding embodiment, wherein the probe is a molecule selected from the group of molecules consisting of a deoxyribonucleic acid (DNA), a peptide nucleic acid (PNA), a locked nucleic acid (LNA), and a ribonucleic acid (RNA).

3. The method of any preceding embodiment, wherein the target probes are anchored to the nanoporous electrodes with a chemical linker.

4. The method of any preceding embodiment, wherein the chemical linker is a linker selected from the group of linkers consisting of a selenol group linker, an amine group linker and a thiol group linker.

5. The method of any preceding embodiment, wherein the washed target-probe hybrids from the nanoporous electrodes are released with cyclic voltammetry (CV) and an electrolyte buffer.

6. The method of any preceding embodiment, further comprising: detecting the presence of target-probe hybrids on the nanoporous electrodes with electrochemistry prior to release.

7. The method of any preceding embodiment, further comprising: analyzing collected target-probe hybrids with fluorescence to determine hybrid concentration, analyzing absorbance to determine a DNA-to-protein concentration ratio, and conducting capillary electrophoresis to determine hybrid size and purity.

8. The method of any preceding embodiment, further comprising: separating the targets from the probes from the collected target-probe hybrids; and purifying the separated targets.

9. The method of any preceding embodiment, further comprising: providing a variety of different types of probe, each probe type coupled to a chemical linker that has a different affinity to the nanoporous electrode; and selectively eluting different probe hybrids by applying different electrochemical potentials over time.

10. The method of any preceding embodiment, further comprising: anchoring a group of a first target probes to the nanoporous electrode with a thiol group linker; anchoring a group of a second target probe to the nanoporous electrode with a selenol group linker; releasing washed first target-probe hybrids from the nanoporous electrodes by electrochemically cleaving the thiol linker of the first target probes; eluting and collecting first target-probe hybrids; releasing washed second target-probe hybrids from the nanoporous electrodes by electrochemically cleaving the selenol linker of the second target probes; and eluting and collecting the second target-probe hybrids.

11. The method of any preceding embodiment, wherein the first target-probe hybrids are iontophoretically eluted.

12. The method of any preceding embodiment, wherein the first target-probe hybrids are passively eluted.

13. The method of any preceding embodiment, wherein the second target-probe hybrids are iontophoretically eluted.

14. The method of any preceding embodiment, wherein the second target-probe hybrids are passively eluted.

15. The method of any preceding embodiment, wherein the washed first target-probe hybrids from the nanoporous electrodes are released with cyclic voltammetry (CV) in a first potential window and the washed second target-probe hybrids from the nanoporous electrodes are released with cyclic voltammetry (CV) in a second potential window.

16. The method of any preceding embodiment, the conductance measurements comprising: binding collected target-probe hybrids to a first nanoscale electrode; repeatedly contacting the bound target-probe hybrid with a second nanoscale electrode; and measuring conductance, wherein nucleic acid matches and mismatches between the target molecule and the probe are detected based on the conductance.

17. The method of any preceding embodiment, wherein conductance based spectroscopic measurements will allow multiple targets to be identified in parallel with a single experimental run.

18. The method of any preceding embodiment, further comprising: compiling a library of conductance measurements of previously tested hybrids; and comparing conductance measurements of subject hybrids with library measurements to identify the subject hybrid by its conduction measurements.

19. The method of any preceding embodiment, further comprising: entering the conductance measurements of a subject hybrid in the library if the subject hybrid measurements are not present in the library.

20. A method for detection and purification of nucleic acids from complex biological samples, the method comprising: (a) selecting at least one target and corresponding probe; (b) anchoring the probes on surfaces of a nanoporous metal electrode; (c) forming target-probe hybrid duplexes on the nanoporous metal electrodes from targets from a sample; (d) washing the nanoporous electrodes and target-probe hybrids to remove any sample parts that are not bound to the target probes; (e) releasing and eluting washed target-probe hybrids from the nanoporous electrodes; (f) collecting eluted target-probe hybrids; and (g) performing conductance measurements of the collected target-probe hybrids.

21. The method of any preceding embodiment, wherein the target probes are anchored to the nanoporous electrodes with a chemical linker selected from the group of linkers consisting of a selenol group linker, an amine group linker and a thiol group linker.

22. The method of any preceding embodiment, further comprising: providing a variety of different types of probe, each probe type coupled to a chemical linker that has a different affinity to the nanoporous electrode; and selectively eluting different probe hybrids by applying different electrochemical potentials over time.

23. The method of any preceding embodiment, further comprising: an array of nanoporous electrodes, each nanoporous electrode having a different probe type grafted to pore surfaces of the electrode.

24. The method of any preceding embodiment, further comprising: separating the targets from the probes from the collected target-probe hybrids; and purifying the separated targets.

25. The method of any preceding embodiment, further comprising: cleaving single-stranded overhangs of DNA or RNA in the duplexes following target-probe hybridization in solution.

26. The method of any preceding embodiment, further comprising: cleaving overhangs of DNA or RNA in the duplexes following target-probe hybridization in situ on nanoporous electrodes.

27. An apparatus for detection and purification of nucleic acids from complex biological samples, comprising: (a) a microfluidic network of channels; (b) at least one nanoporous metal electrode disposed within a channel of the microfluidic network; (c) a plurality of probes grafted into pores of the nanoporous electrode with a linker; and (d) a single molecule break-junction detector.

28. The apparatus of any preceding embodiment, further comprising: (a) a processor; and (b) a non-transitory memory storing instructions executable by the processor; (c) wherein the instructions, when executed by the processor, perform steps comprising: (i) detecting the presence of hybrids on the nanoporous electrodes; (ii) releasing target-probe hybrids from the nanoporous electrodes with cyclic voltammetry (CV); (iii) repeatedly contacting target-probe hybrids bound to a first nanoscale electrode with a second nanoscale electrode; (iv) measuring conductance, wherein nucleic acid matches and mismatches between the target molecule and the probe are detected based on the conductance; (v) comparing conductance measurements of subject hybrids with a library of conductance measurements to identify the subject hybrid by its conduction measurements; and (vi) identifying the target.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method for detection and purification of nucleic acids from complex biological samples, the method comprising:
   (a) selecting at least one target and corresponding target probe;
   (b) forming target-probe hybrid duplexes from targets from a sample;
   (c) capturing formed target-probe hybrid duplexes on one or more nanoporous metal electrodes;
   (d) washing the one or more nanoporous metal electrodes and captured target-probe duplexes to remove any sample parts that are not bound to the target-probe duplexes;
   (e) releasing and eluting washed target-probe hybrid duplexes from the one or more nanoporous metal electrodes;
   (f) purifying the eluted target-probe hybrid duplexes; and
   (g) performing conductance measurements of the purified target-probe hybrid duplexes.

2. The method of claim 1, wherein the target probe is a molecule selected from the group of molecules consisting of a deoxyribonucleic acid (DNA), a peptide nucleic acid (PNA), a locked nucleic acid (LNA), and a ribonucleic acid (RNA).

3. The method of claim 1, wherein each target probe is anchored to the one or more nanoporous metal electrodes with a chemical linker.

4. The method of claim 3, wherein the chemical linker is a linker selected from the group of linkers consisting of a selenol group linker, an amine group linker and a thiol group linker.

5. The method of claim 1, wherein said washed target-probe hybrid duplexes from the one or more nanoporous metal electrodes are released with cyclic voltammetry (CV) and an electrolyte buffer.

6. The method of claim 1, further comprising:
   detecting the presence of target-probe duplexes on said one or more nanoporous metal electrodes with electrochemistry prior to release.

7. The method of claim 1, further comprising:
   analyzing purified target-probe hybrid duplexes with fluorescence to determine hybrid duplex concentration; and
   conducting capillary electrophoresis to determine hybrid duplex size and purity.

8. The method of claim 1, further comprising:
   separating targets from target probes from the purified target-probe duplexes; and
   collecting the separated targets.

9. The method of claim 1, further comprising:
providing a variety of different types of target probes, each target probe type coupled to a chemical linker that has a different affinity to a nanoporous metal electrode;
binding said chemical linkers to said nanoporous metal electrode;
selectively eluting different linked target-probe hybrid duplexes by applying different electrochemical potentials to the nanoporous metal electrode over time.

10. The method of claim 1, further comprising:
anchoring a group of a first target probe to one or more nanoporous metal electrodes with a thiol group linker;
anchoring a group of a second target probe to the one or more nanoporous metal electrodes with a selenol group linker;
releasing washed first target-probe hybrid duplexes from the one or more nanoporous metal electrodes by electrochemically cleaving the thiol group linker of the first target probes;
eluting and collecting released first target-probe hybrid duplexes;
releasing washed second target-probe hybrid duplexes from the one or more nanoporous metal electrodes by electrochemically cleaving the selenol group linker of the second target probes; and
eluting and collecting the released second target-probe hybrid duplexes.

11. The method of claim 10, wherein said washed first target-probe hybrid duplexes from the one or more nanoporous metal electrodes are released with cyclic voltammetry (CV) in a first potential window and said washed second target-probe hybrid duplexes from the one or more nanoporous metal electrodes are released with cyclic voltammetry (CV) in a second potential window.

12. The method of claim 1, said conductance measurements comprising:
binding at least one purified target-probe hybrid duplex to a first nanoscale metal electrode;
repeatedly contacting the bound target-probe hybrid duplex with a second nanoscale metal electrode; and
measuring conductance, wherein any nucleic acid matches and mismatches between the target molecule and the target probe are detected based on said conductance.

13. The method of claim 12, further comprising:
performing conductance based spectroscopic measurements on a plurality of purified target-probe hybrid duplexes;
wherein conductance based spectroscopic measurements allow multiple targets to be identified in parallel with a single experimental run.

14. The method of claim 1, further comprising:
compiling a library of conductance measurements of previously tested target- probe hybrid duplexes; and
comparing conductance measurements of a subject target-probe hybrid duplex with library measurements to identify the subject target-probe hybrid duplex by its conduction measurements.

15. The method of claim 14, further comprising:
entering the conductance measurements of the subject target-probe hybrid duplexes in the library if the subject hybrid duplex measurements are not present in the library.

16. The method of claim 1, further comprising:
separating targets from target probes from the purified target-probe hybrid duplexes; and
purifying the separated targets.

* * * * *